United States Patent [19]

Kumar et al.

[11] Patent Number: 4,734,404
[45] Date of Patent: Mar. 29, 1988

[54] PESTICIDAL BENZOYLUREIDOARYL PHOSPHATE COMPOUNDS

[75] Inventors: Raaj Kumar, Bhopal, India; Themistocles D. J. D'Silva, Chapel Hill, N.C.

[73] Assignee: Rhone-Poulenc Nederland B.V., Amstelveen, Netherlands

[21] Appl. No.: 871,253

[22] Filed: Jun. 6, 1986

[51] Int. Cl.$^4$ .......................... A01N 57/06; C07F 9/18
[52] U.S. Cl. ..................................... 514/115; 558/190
[58] Field of Search ......................... 558/190; 514/115

[56] References Cited

U.S. PATENT DOCUMENTS 4,005,223  1/1977  Sirrenberg et al. ................. 424/322
4,041,177  8/1977  Sirrenberg et al. ................. 424/322
4,068,002  1/1978  Sirrenberg et al. ................. 424/322
4,183,922  1/1980  Taylor .................................. 558/190

FOREIGN PATENT DOCUMENTS 8109495  6/1983  Japan .

OTHER PUBLICATIONS

Abstract of Japanese 8109495, granted 6/29/83.

Primary Examiner—Anton H. Sutto
Attorney, Agent, or Firm—Morgan & Finnegan

[57] ABSTRACT

Novel benzoylureidoaryl phosphate compounds are provided together with methods for their preparation and the use of said compounds as the active toxicant in pesticidal compositions.

9 Claims, No Drawings

PESTICIDAL BENZOYLUREIDOARYL PHOSPHATE COMPOUNDS

BRIEF SUMMARY OF THE INVENTION

1. Technical Field

This invention relates to novel benzoylureidoaryl phosphate compounds which are useful as the active toxicant in pesticidal compositions. This invention also relates to a method for preparation of the novel benzoylureidoaryl phosphate compounds. This invention further relates to pesticidal compositions and to a method for their use.

2. Background of the Invention

In recent years, a variety of benzoyl urea compounds have been reported in the literature as having pesticidal activity. For example, benzoylureido-diphenyl ethers and their use as insecticides have been disclosed in U.S. Pat. Nos. 4,005,223 issued Jan. 25, 1977, 4,041,177 issued Aug. 9, 1977, and 4,068,002 issued Jan. 10, 1978. Also benzoyl(thio)ureido(thio)phosphoric acid ester derivative compounds and their use as insecticides and miticides have been disclosed in Japanese Patent Application No. 5 8109 495 published June 29, 1983.

However, benzoylureidoaryl phosphate compounds of this invention and their use as the active toxicant in pesticidal compositions have not been disclosed in the art.

Accordingly, it is an object of this invention to provide novel benzoylureidoaryl phosphate compounds. Another object of this invention is to provide benzoylureidoaryl phosphate compounds which exhibit excellent pesticidal activity. A further object is to provide processes for the preparation of the novel benzoylureidoaryl phosphate compounds. A still further object is to provide novel pesticidal compositions containing the novel benzoylureidoaryl phosphate compounds as the active toxicant. Another object of this invention is to provide a method for controlling pests by the application of the novel benzoylureidoaryl phosphate compounds. These and other objects will readily become apparent to those skilled in the art in light of the teachings herein set forth.

DISCLOSURE OF THE INVENTION

This invention relates to novel benzoylureidoaryl phosphate compounds, pesticidal compositions containing the same, and processes for their preparation and use. The benzoylureidoaryl phosphate compounds of this invention can be represented by the following formula:

FORMULA 1

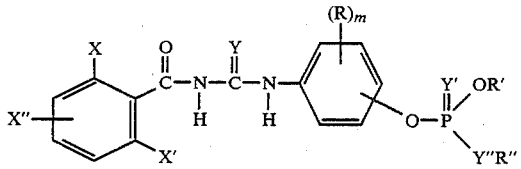

wherein:

X, X' and X" are independently hydrogen, halogen, alkyl, haloalkyl, polyhaloalkyl, alkoxy, haloalkoxy or polyhaloalkoxy;

Y, Y' and Y" are independently oxygen or sulfur;

R is halogen, alkyl, haloalkyl, polyhaloalkyl or polyhaloalkoxy;

m is a value of from 0 to 3; and

R' and R" are independently alkyl which may be a straight or branched chain.

DETAILED DESCRIPTION

As indicated above, this invention relates to novel benzoylureidoaryl phosphate compounds, pesticidal compositions containing the same, and processes for their preparation and use.

Preferred benzoylureidoaryl phosphate compounds within the generic Formula (1) are those having the formulae:

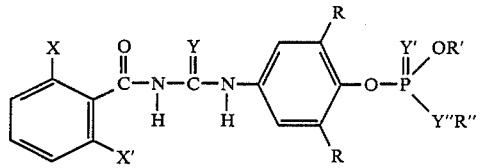

wherein X, X', Y, Y', Y", R, R' and R" are as defined above; and

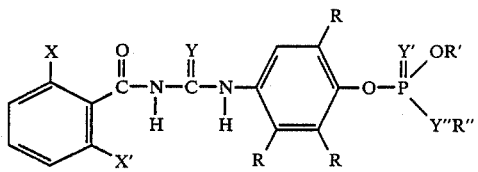

wherein X, X', Y, Y', Y", R, R' and R" are as defined above.

Particularly preferred benzoylureidoaryl phosphate compounds are those of the formulae:

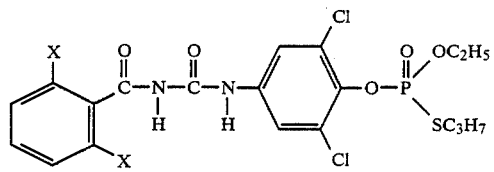

wherein X and X' are as defined above; and

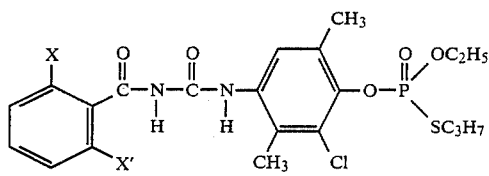

wherein X and X' are as defined above.

Illustrative benzoylureidoaryl phosphate compounds within the scope of Formula 1 which can be used as the active toxicant in pesticidal compositions and which can be prepared by the practice of this invention are as follows:

1-[2,5-dichloro-4-(O-ethyl-S-propylphosphoryloxy)-phenyl]-3-(2,6-difluorobenzoyl)urea;

1-[2,6-dimethyl-4-(O-ethyl-S-propylphosphoryloxy)-phenyl]-3-(2-chlorobenzoyl)urea;

1-[2,5-dimethyl-3-chloro-4-(O-ethyl-S-propylphosphoryloxy)phenyl]-3-(2,6-difluorobenzoyl)urea;
1-[2-methyl-3-chloro-4-(O-ethyl-S-propylphosphoryloxy)phenyl]-3-(2-chlorobenzoyl)urea;
1-[2-methyl-4-(O-ethyl-S-sec-butylphosphoryloxy)phenyl]-3-(2,6-difluorobenzoyl)urea;
1-[3-(O-ethyl-S-propylphosphoryloxy) phenyl]-3-(2,6-difluorobenzoyl)urea;
1-[4-chloro-3-(O-ethyl-S-propylphosphoryloxy) phenyl]-3-(2,6-difluorobenzoyl)urea;
1-[2-methyl-4-(O-ethyl-S-propylphosphoryloxy) phenyl]-3-(2-chlorobenzoyl) thiourea;
1-[2-methyl-4-(O-ethyl-S-propylphosphoryloxy) phenyl]-3-(2,6-dimethoxybenzoyl)urea;
1-[3-methyl-4-(O-ethyl-S-propylphosphoryloxy) phenyl]-3-(2-chlorobenzoyl)urea;
1-[3-methyl-4-(O-ethyl-S-propylphosphoryloxy) phenyl]-3-(2,6-difluorobenzoyl)urea;
1-[-4-(O-ethyl-S-propylphosphoryloxy) phenyl]-3-(2,6-difluorobenzoyl)urea;
1-[4-(O-ethyl-S-propylphosphoryloxy) phenyl]-3-(2-chlorobenzoyl)urea;
1-[4-(O-ethyl-S-propylphosphoryloxy) phenyl]-3-(2-trifluoromethylbenzoyl)urea;
1-[3,5 -dichloro-4-(O-ethyl-S-propylphosphoryloxy)-phenyl]-3-(2-chlorobenzoyl)urea;
1-[4-(O-ethyl-S-propylphosphoryloxy)phenyl]-3-(2,6-dichlorobenzoyl)urea;
1-[3,5-dichloro-4-(O,O-diethylphosphoryloxy)phenyl]-3-(2,6-difluorobenzoyl)urea;
1-[3,5-dichloro-4-(O-ethyl-S-sec-butylphosphoryloxy)-phenyl]-3-(2,6-difluorobenzoyl)urea; and
1-[3,5-dichloro-4-(O-ethyl-S-butylphosphoryloxy)-phenyl]-3-(2,6-difluorobenzoyl)urea.

It is appreciated that the particular compounds listed hereinabove are illustrative of benzoylureidoaryl phosphate compounds of this invention. This invention is not to be construed as being limited only to these compounds; but rather, this invention includes those benzoylureidoaryl phosphate compounds encompassed within Formula 1 hereinabove.

The novel benzoylureidoaryl phosphate compounds of this invention can be conveniently prepared by one or more methods. For example, the compounds of this invention can be prepared by reacting a substituted aniline 2 with a benzoyl isocyanate 3 according to Scheme I as follows:

Scheme I

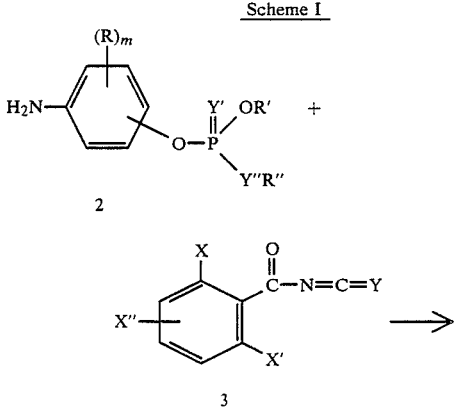

Scheme I

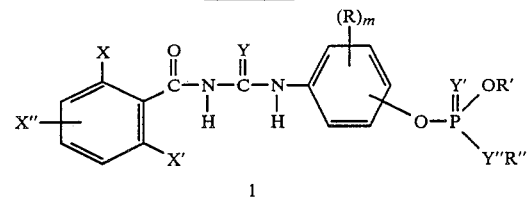

wherein X, X', X", Y, Y', Y", R, R', R" and m have the meaning given in Formula 1.

Alternatively, the novel benzoylureidoaryl phosphate compounds may be prepared by the reaction of a substituted phenylisocyanate 4 with a benzamide 5 according to Scheme II as follows:

Scheme II

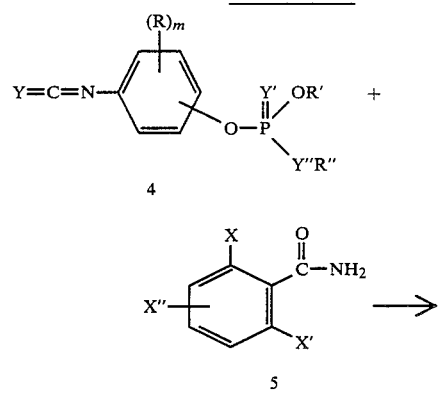

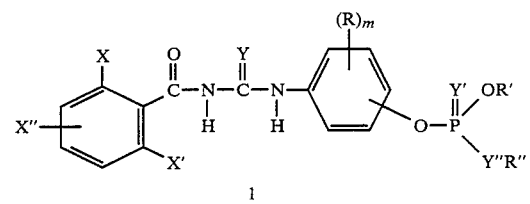

wherein X, X', X", Y, Y', Y", R, R', R" and m have the meaning given in Formula 1.

The benzoylureidoaryl phosphate compounds may also be prepared by the reaction of a benzoylurea 6 with a phosphorochloridate 7 according to Scheme III as follows:

Scheme III

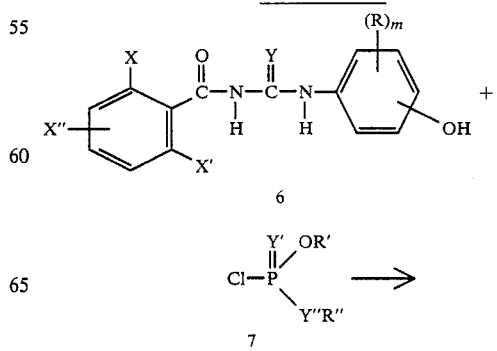

-continued
Scheme III

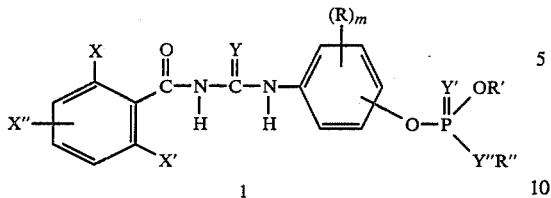

wherein X, X', X", Y, Y', Y", R, R', R" and m have the meaning given in Formula 1.

In general, the reactions illustrated in Schemes I, II and III can be carried out in organic solvents such as aromatic hydrocarbons, halogenated hydrocarbons, ethers and the like. Solvents like toluene, 1,2-dichloroethane, dichloromethane and p-dioxane are preferred. These reactions proceed at temperatures ranging from ambient temperature to 150° C.

The intermediates shown in Schemes I, II and III can be prepared according to generally accepted procedures. Thus, the benzoyl isocyanate 3 can be prepared from the corresponding benzamide 5 following the general procedure of Speziale et al., *J. Org. Chem.* 27, 3742 (1962) as follows:

Scheme IV

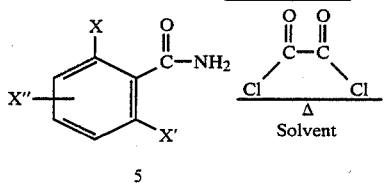

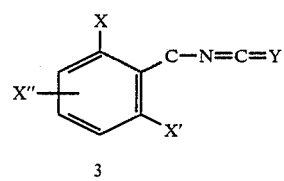

wherein X, X' and X" have the meaning given in Formula 1.

The substituted aniline 2 can be prepared according to Scheme V involving the reaction of a substituted nitrophenol 8 with a phosphorochloridate 7 as follows:

Scheme V

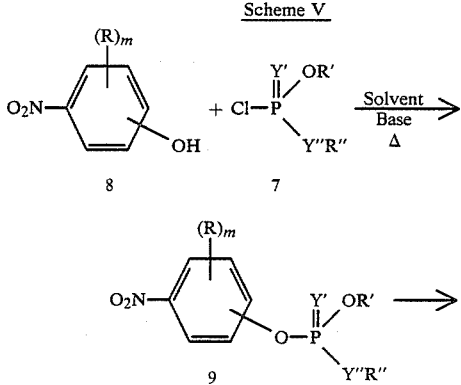

-continued
Scheme V

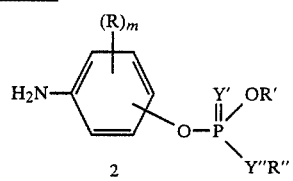

wherein Y', Y", R, R', R" and m have the meaning given in Formula 1. The reaction of a substituted nitrophenol 8 with a phosphorochloridate 7 to give the nitrophenyl phosphate 9 proceeds in the presence of a base in an inert solvent at elevated temperature. Bases suitable for this reaction are potassium carbonate, sodium hydride, potassium hydroxide, and sodium hydroxide. Suitable solvents are toluene, dimethylformamide, and dimethylsulfoxide. The above transformation can be carried out in a diphasic reaction medium in the presence of a phase-transfer catalyst. The preparation of nitrophenyl phosphate 9 is more fully described in U.S. Pat. Nos. 3,954,919, 3,705,218 and 4,027,018.

The reduction of nitrophenyl phosphate 9 to substituted aniline 2 can be achieved by chemical reduction utilizing iron and ethanolic aqueous hydrochloric acid. The reduction may also be achieved by hydrogenation using a catalytic amount of platinum or palladium on carbon under an atmosphere of hydrogen at a pressure ranging from 40–200 psi at ambient temperature. Suitable solvents for hydrogenation include aromatic hydrocarbons or alcohols. The reduction may further be achieved by a chemical method using hydrazine and a metal catalyst as disclosed in *Chem. Rev.*, Vol. 65, pp. 51–68 (1965).

Substituted phenylisocyanate 4 can be obtained by reacting substituted aniline 2 with phosgene according to Scheme VI as follows:

Scheme VI

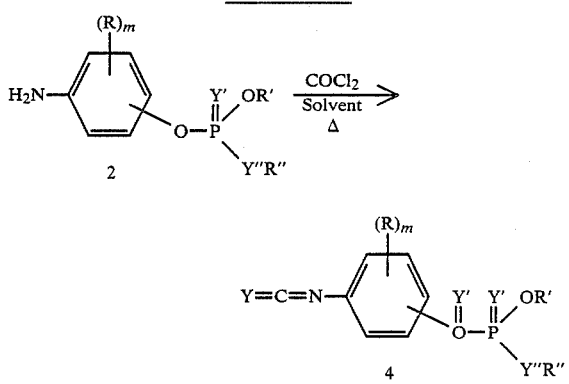

wherein Y, Y', Y", R, R', R" and m have the meaning given in Formula 1.

Benzoylureas of type 6 can be prepared by reacting benzoylisocyanate 3 with aminophenol 10 according to Scheme VII as follows:

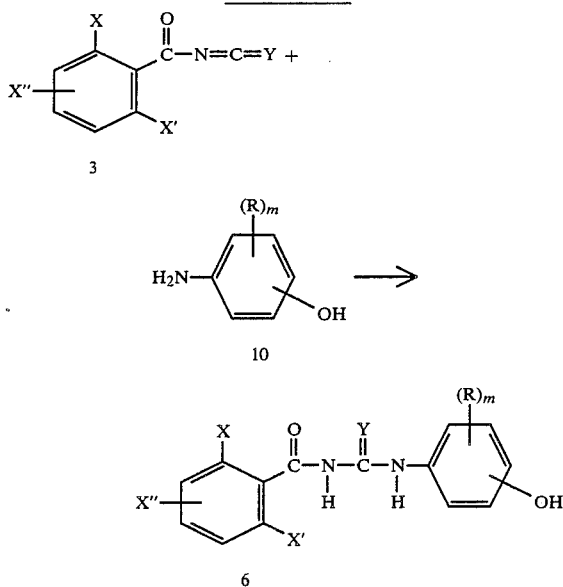

Scheme VII wherein X, X', X", Y, R and m have the meaning given in Formula 1.

Phosphorochloridates of type 7 are commercially available and can be prepared by conventional methods known in the art.

The benzoylureidoaryl phosphate compounds contemplated in this invention may be employed as pesticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, nitrobenzene, cyclohaxanone or dimethyl formamide and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultraviolet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are now compatible with substantially any other constituents of the spray schedule, and they may be used in the soil, upon the seed, or the roots of plants without injuring either the seeds or roots of plants. Mixtures of the active compounds may be employed if desired as well as combinations of the active compounds of this invention with other biologically active compounds or ingredients.

The following examples are illustrative of the methods utilized in the preparation of intermediates and compounds of this invention.

EXAMPLE A

Preparation of 1-(3,5-dichloro-4-hydroxyphenyl)-3-(2-chlorobenzoyl)urea

Into a reaction flask containing 6.23 grams (35.0 mmol) of 2,6-dichloro-4-aminophenol in 100 milliliters of toluene (heated to a temperature of 100° C. to dissolve the solid) was added with continuous stirring a solution of 7.63 grams (42.0 mmol) of 2-chlorobenzoyl isocyanate dissolved in 25 milliliters of toluene. The resulting exothermic reaction raised the temperature to boiling with the formation of a solid precipitate. Additional amounts of toluene were added to the reaction flask to facilitate stirring until the addition of 2-chlorobenzoyl isocyanate was complete. After cooling to ambient temperature, the solid precipitate was filtered and the residue was washed successively with toluene and hexane and air dried to afford 11.99 grams of 1-(3,5-dichloro-4-hydroxyphenyl)-3-(2-chlorobenzoyl)urea as a light brown solid having a melting point of 220° C.–222° C. Elemental analysis of the light brown solid indicated the following:

Analysis: $C_{14}H_9Cl_3N_2O_3$. Calculated: C, 46.76; H, 2.52; N, 7.79. Found: C, 47.23; H, 2.68; N, 7.93.

EXAMPLE B

Preparation of 1-(3,5-dichloro-4-hydroxyphenyl)-3-(2,6-difluorobenzoyl)urea

In a manner similar to the procedure employed in Example A except that 2,6-difluorobenzoyl isocyanate was used instead of of 2-chlorobenzoyl isocyanate, 1-(3,5-dichloro-4-hydroxyphenyl)-3-(2,6-difluorobenzoyl)urea was prepared having a melting point of 196°

C.–197° C. Elemental analysis of the product indicated the following:

Analysis: $C_{14}H_8Cl_2F_2N_2O_3$. Calculated: C, 46.58; H, 2.23; N, 7.76. Found: C, 47.19; H, 2.63; N, 7.66.

EXAMPLE C

Preparation of 1-(2,5-dimethyl-3-chloro-4-hydroxyphenyl-3-(2-6-difluorobenzoyl)urea Into a reaction flask containing 1.9 grams (11.0 mmol) of 2,5-dimethyl-6-chloro-4-aminophenol in 100 milliliters of dichloromethane was added 2.23 grams (12.2 mmol) of 2,6-difluorobenzoyl isocyanate. After stirring at ambient temperature for one hour, the resulting precipitate was filtered to afford 3.44 grams of 1-(2,5-dimethyl-3-chloro-4-hydroxyphenyl)-3-(2,6-difluorobenzoyl)urea having a melting point of 218° C.–219° C. Elemental analysis of the product indicated the following:

Analysis: $C_{16}H_{13}ClF_2N_2O_3$. Calculated: C, 54.17; H, 3.69; N, 7.90. Found: C, 53.79; H, 3.72; N, 7.77.

EXAMPLE D

Preparation of 2,5-dimethyl-6-chloro-4-aminophenol

Into a Parr bottle containing 5.0 grams (24.8 mmol) of 2,5-dimethyl-6-chloro-4-nitrophenol in 40 milliliters of ethyl alcohol was added 0.5 grams of 5 percent platinum on carbon. This mixture was hydrogenated for 45 minutes in a Parr apparatus. The resulting solution was filtered over charcoal and Celite and the solvent was evaporated to afford 4.09 grams of 2,5-dimethyl-6-chloro-4-aminophenol having a melting point of 127° C.–128° C. Recrystallization from ethyl acetate and hexane afforded a product having a melting point of 129° C.–130° C. Elemental analysis of the product indicated the following:

Analysis: $C_8H_{10}ClNO$. Calculated: C, 55.99; H, 5.87; N, 8.16 Found: C, 56.23; H, 6.02; N, 8.03.

EXAMPLE 1

Preparation of 1-[2-methyl-3,5-dichloro-4-(O-ethyl-S-propylphosphoryloxy)phenyl]-3-(2,6-difluorobenzoyl)urea Into a reaction flask containing 0.27 grams (0.754 mmol) of 2-methyl-3,5-dichloro-4-(O-ethyl-S-propylphosphoryloxy)aniline in 10 milliliters of dichloromethane was added 0.152 grams (0.83 mmol) of 2,6-difluorobenzoyl isocyanate. The resulting mixture was stirred for a period of 19 hours at ambient temperature. After the stirring period, the solvent was evaporated to afford 0.34 grams of 1-[2-methyl-3,5-dichloro-4-(O-ethyl-S-propylphosphoryloxy)phenyl]-3-(2,6-difluorobenzoyl)urea having a melting point of 170.5° C.–172.5° C. Elemental analysis of the product indicated the following:

Analysis: $C_{20}H_{21}Cl_2F_2O_5PS$. Calculated: C, 44.38; H, 3.91; N, 5.17. Found: C, 44.31; H, 3.94; N, 5.13.

EXAMPLE 2

Preparation of 1-[3,5-dichloro-4-(O-ethyl-S-propylphosphoryloxy)phenyl]-3-(2,6-difluorobenzoyl) urea Into a reaction flask containing a slurry of 0.38 grams (1.05 mmol) of 1-(3,5-dichloro-4-hydroxyphenyl)-3-(2,6-difluorobenzoyl) urea in dichloromethane was added 0.13 grams (1.26 mmol) of triethylamine and 0.24 grams (1.16 mmol) of O-ethyl-S-propylphosphorochloridate. The resulting mixture was stirred for a period of about 18 hours at ambient temperature. The mixture was then further diluted with dichloromethane, washed with water, and the organic phase separated, dried and concentrated. Recrystallization from ethyl acetate of the resulting product afforded 0.25 grams of 1-[3,5-dichloro-4-(O-ethyl-S-propylphosphoryloxy)phenyl]-3-(2,6-difluorobenzoyl) urea as a white solid having a melting point of 149° C.–151° C. Elemental analysis of the white solid indicated the following:

Analysis: $C_{19}H_{19}Cl_2F_2N_2O_5PS$. Calculated: C, 43.28; H, 3.63; N, 5.31. Found: C, 43.44; H, 3.71; N, 5.21.

EXAMPLES 3–17

In a manner similar to that employed in the preceding examples, and using one of the synthesis schemes previously disclosed, other benzoylureidoaryl phosphate compounds were prepared. The identity of the particular compounds and the analytical data are set forth in Table I below.

TABLE I

Representative Benzoylureidoaryl Phosphate Compounds

| Example | Structure | Calculated C | Calculated H | Calculated N | Found C | Found H | Found N | Melting Point °C. |
|---|---|---|---|---|---|---|---|---|
| 3 | | 52.01 | 5.40 | 5.78 | 52.01 | 5.32 | 5.70 | 133.5–134.5 |
| 4 | | 49.78 | 4.62 | 6.11 | 50.08 | 4.63 | 6.07 | 158–159 |

TABLE I-continued

Representative Benzoylureidoaryl Phosphate Compounds

| Example | Structure | Elemental Analysis Calculated | | | Found | | | Melting Point °C. |
|---------|-----------|---|---|---|---|---|---|---|
|         |           | C | H | N | C | H | N |   |
| 5  | 2,6-difluorobenzoyl-N-C(O)-N-H; 2,5-dichlorophenyl-O-P(O)(OC$_2$H$_5$)(SC$_3$H$_7$) | 43.28 | 3.63 | 5.31 | 43.97 | 3.64 | 5.54 | 149–151 |
| 6  | 2-chlorobenzoyl-N-C(O)-N-H; 2,5-dichlorophenyl-O-P(O)(OC$_2$H$_5$)(SC$_3$H$_7$) | 43.40 | 3.83 | 5.33 | 43.36 | 3.93 | 5.22 | 132–134 |
| 7  | 2,6-difluorobenzoyl-N-C(O)-N-H; 2,6-dimethylphenyl-O-P(O)(OC$_2$H$_5$)(SC$_3$H$_7$) | 51.85 | 5.18 | 5.76 | 52.60 | 5.50 | 5.63 | Oil |
| 8  | 2-chlorobenzoyl-N-C(O)-N-H; 2,6-dichlorophenyl-O-P(O)(OC$_2$H$_5$)(SC$_3$H$_7$) | 43.40 | 3.83 | 5.33 | 43.80 | 3.94 | 5.43 | 128–130 |
| 9  | 2-chlorobenzoyl-N-C(O)-N-H; 2,6-dimethyl-3-chlorophenyl-O-P(O)(OC$_2$H$_5$)(SC$_3$H$_7$) | 48.56 | 4.85 | 5.39 | 48.52 | 4.82 | 5.36 | 151.5–152 |
| 10 | 2-chlorobenzoyl-N-C(O)-N-H; 2,6-dichlorophenyl-O-P(O)(OC$_2$H$_5$)$_2$ | 43.62 | 3.66 | 5.65 | 44.43 | 3.82 | 5.40 | 169–171 |
| 11 | 2,6-difluorobenzoyl-N-C(O)-N-H; 2,5-dichlorophenyl-O-P(O)(OC$_2$H$_5$)$_2$ | 43.48 | 3.45 | 5.63 | 43.51 | 3.56 | 5.50 | 165–168 |
| 12 | 2,6-difluorobenzoyl-N-C(O)-N-H; 3-methylphenyl-O-P(O)(OC$_2$H$_5$)(SC$_3$H$_7$) | 50.85 | 4.91 | 5.93 | 51.23 | 4.84 | 6.07 | 99–101 |

TABLE I-continued
Representative Benzoylureidoaryl Phosphate Compounds

| Example | Structure | Elemental Analysis Calculated C | H | N | Found C | H | N | Melting Point °C. |
|---|---|---|---|---|---|---|---|---|
| 13 | [2-Cl-C6H4-C(O)-NH-C(O)-NH-(3-CH3-C6H3)-O-P(O)(OC2H5)(SC3H7)] | ¹HNMR (CDCl₃) δ 0.98(t, J = 7 Hz, 3H), 1.28-2.0 (m, 5H), 2.3 (d, J = 1 Hz, 3H), 2.62-3.10 (m, 2H), 4.03-4.53 (m, 2H), 7.0-8.1 (m, 7H), 9.7 (NH), 10.57 (NH). | | | | | | Oil |
| 14 | [2,6-F2-C6H3-C(O)-NH-C(O)-NH-(2,5-(CH3)2-C6H2)-O-P(O)(OC2H5)(SC3H7)] | 51.85 | 5.18 | 5.76 | 51.94 | 5.05 | 5.66 | Oil |
| 15 | [2-Cl-C6H4-C(O)-NH-C(O)-NH-(2,5-(CH3)2-C6H2)-O-P(O)(OC2H5)(SC3H7)] | 52.01 | 5.40 | 5.78 | 52.26 | 5.50 | 5.76 | 118-120 |
| 16 | [2,6-F2-C6H3-C(O)-NH-C(O)-NH-C6H4-O-P(O)(OC2H5)(SC3H7)] | 49.78 | 4.62 | 6.11 | 49.78 | 4.93 | 5.61 | 126-128 |
| 17 | [2-Cl-C6H4-C(O)-NH-C(O)-NH-C6H4-O-P(O)(OC2H5)(SC3H7)] | ¹HNMR (CDCl₃) δ 0.95 (t, J = 7 Hz, 3H), 1.27-2.0 (m, 5H), 2.62-3.12 (m, 2H), 4.03-4.57 (m, 2H), 7.03-7.97 (m, 7H), 8.63 (s, 1H), 9.8 (s, NH), 10.93 (s, NH). | | | | | | |

Suspensions of the test compounds were prepared by dissolving 100 milligrams of compound in 1.5 milliliters of dimethylformamide and then adding 8.5 milliliters of an acetone solution containing 0.25 percent of an alkylphenoxy polyethoxyethanol surfactant, as an emulsifying or dispersing agent. The resulting solution was mixed into 30 milliliters of water to give roughly 40 milliliters of a suspension containing the compound in finely divided form. The thus-prepared stock suspension contained 2.5 percent by weight of compound. The test concentrations in parts per million by weight employed in the tests described hereinbelow were obtained by appropriate dilutions of the stock suspension with water. Sonication was used where necessary to obtain a homogeneous suspension. The test procedures were as follows:

SOUTHERN ARMYWORM LEAF SPRAY TEST

Larvae of the southern armyworm (*Spodoptera eridania*, (Cram.)), reared on Tendergreen bean plants at a temperature of 80°±5° F. and a relative humidity of 50±5 percent, constituted the test insects.

The test compounds were formulated by diluting the stock suspension with water to give a suspension containing the test compound at the concentrations (in parts of the test compound per million parts of final formulation) as set forth in Table II below. Potted tendergreen bean plants of standard height and age were placed on a revolving turntable and sprayed with 100 milliliters of test compound formulation by use of a DeVilbiss spray gun set at 40 psig air pressure. This application, which lasted 25 seconds, was sufficient to wet plants to run-off. As a control, 100 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°-85° F. for five days. Although the larvae could easily consume the whole left within twenty-four hours, no more food was added. Larvae which were unable to move the length of the body, even upon stimulation by prodding, were considered dead. Percent mortality was recorded for various concentration levels.

MEXICAN BEAN BEETLE LEAF SPRAY TEST

Third instar larvae of the Mexican bean beetle (*Ephilachna varivestis*, Muls.), reared on Tendergreen bean plants at a temperature of 80°±5° F. and 50±5 percent relative humidity, were the test insects.

The test compounds were formulated by diluting the stock suspension with water to give a suspension containing the test compound at the concentrations (in parts of the test compound per million parts of final formulation) as set forth in Table II below. Potted Tendergreen bean plants of standard height and age were placed on a revolving turntable and sprayed with 100 milliliters of test compound formulation by use of a DeVilbiss spray gun set at 40 psig air pressure. This application, which lasted 25 seconds, was sufficient to wet plants to run-off. As a control, 100 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F., for five days. Although the larvae could easily consume the left within 24 to 48 hours, no more food was added. Larvae which were unable to move the length of the body, even upon stimulation, were considered dead. Percent mortality was recorded for various concentration levels.

MITE LARVACIDAL TEST METHOD

The eggs of the two-spotted mite (*Tetranychus urticae* (Koch)) were obtained from adults reared on Tendergreen beans under controlled conditions (80°±5° F. and 50±5 percent relative humidity). Heavily infested leaves from the stock culture were placed on uninfested bean plants. Females were allowed to oviposit for a period of 24 hours, and the leaves of the plant were then dipped in a 1000 ppm solution of tetraethylpyrophosphate (TEPP) in order to kill the motile forms and prevent additional egg laying. TEPP does not affect the viability of the eggs. The TEPP treated mite infested plants were held at 80°±5° F. and 50±5 percent relative humidity until the eggs hatch in 3–4 days. Then the larvae were transferred to bean plants 6–8 inches in height. A sufficient number of larvae for testing (50–100) were transferred from TEPP treated leaves to the fresh plants in 24 hours.

Infested Tendergreen bean plants were placed on a revolving turntable. Test compounds were formulated with DMF, acetone, and a 3 to 1 mixture of Triton 172 and 152 (alkylphenoxy polyethoxyethanol surfactant mixture), respectively and then diluted in water to appropriate concentrations of chemical for application to the infested plants by use of a DeVilbiss spray gun with air pressure set at 40 pounds. The volume of 100 milliliters was sufficient to wet the plants to run off. A blank formulation was used for the control.

The treated plants were held at 80°±5° F. and 50±5 percent relative humidity for a period of five to six days, when mortality counts of the larvae were made. Percent mortality was recorded for various concentrations levels.

FLY BAIT TEST

Four to six day old adult house flies (*Musca domestica*, L.), reared according to the specifications of the Chemical Specialities, Manufacturing Association (Blue Book, McNair-Dorland Company, New York, 1954; pages 243–244, 261) under controlled conditions of 80°±5° F. and 50±5 percent relative humidity, were the test insects. The flies were immobilized by anesthetizing with carbon dioxide and 25 immobilized individuals, males and females, were transferred to a cage consisting of a standard food strainer about 5 inches in diameter which was inverted over a wrapping-paper-covered surface. The test compounds were formulated by diluting the stock suspension with a 10 percent (by weight) sugar solution to give a suspension containing 100 parts of test compound per million parts of final formulation, by weight. Ten milliliters of the test formulation were added to a souffle cup containing a one-inch square of an absorbent cotton pad. This bait cup was introduced and centered on the blotting paper under the good strainer prior to admitting the anesthetized flies. The caged flies were allowed to feed on the bait for 24 hours, at a temperature of 80°±5° F. and a relative humidity of 50±5 percent. Flies which showed no sign of movement on prodding were considered dead. Percent mortality was recorded for various concentration levels.

The biological properties of certain representative examples of the benzoylureidoaryl phosphate compounds of this invention are set forth in Table II below.

TABLE II

| Biological Properties of Representative Benzoylureidoaryl Phosphate Compounds | | | | |
|---|---|---|---|---|
| | Biological Activity at 100 ppm* | | | |
| Compound Prepared in Example No. | Southern Armyworm | Mexican Bean Beetle | Mite | House Fly |
| 1 | A | A | C | C |
| 2 | A | A | C | C |
| 3 | A | A | C | A |
| 4 | A | A | C | A |
| 5 | A | A | C | A |
| 6 | A | A | C | C |
| 7 | A | A | C | A |
| 8 | A | A | C | A |
| 9 | A | A | C | C |
| 10 | B | B | C | C |
| 11 | C | A | C | B |
| 12 | A | A | C | C |
| 13 | A | A | A | A |
| 14 | A | A | C | A |
| 15 | A | A | C | A |
| 16 | A | A | B | C |
| 17 | A | A | C | A |

*Code:
A = 71–100% Mortality
B = 31–70% Mortality
C = 0–30% Mortality

The results in Table II demonstrate broad spectrum pesticidal activity for representative benzoylureidoaryl phosphate compounds of this invention including activity against adult house flies.

Although the invention has been illustrated by the foregoing examples, it is not to be construed as being limited to the materials employed therein; but rather, the invention encompasses the generic area as hereinabove disclosed. Various modifications and embodiments can be made without departing from the spirit and scope thereof.

We claim:

1. The compound which is 1-[3,5-dichloro-4-(O-ethyl-S-propylphosphoryloxy)phenyl]-3-(2,6-difluorobenzoyl)urea.

2. A method of controlling pests which comprises subjecting said pests to a pesticidally effective amount of the compound of claim 1.

3. A pesticide composition comprising an acceptable carrier and a pesticidally effective amount of the compound of claim 1.

4. The compound which is 1-[2-methyl-4-(O-ethyl-S-propylphosphoryloxy)phenyl]-3-(2,6-difluorobenzoyl)urea.

5. A method of controlling pests which comprises subjecting said pests to a pesticidally effective amount of the compound of claim 4.

6. A pesticide composition comprising an acceptable carrier and a pesticidally effective amount of the compound of claim 4.

7. The compound which is 1-[2,5-dimethyl-3-chloro-4-(O-ethyl-S-propylphosphoryloxy)phenyl]-3-(2,6-difluorobenzoyl)urea.

8. A method of controlling pests which comprises subjecting said pests to a pesticidally effective amount of the compound of claim 7.

9. A pesticide composition comprising an acceptable carrier and a pesticidally effective amount of the compound of claim 7.

* * * * *